United States Patent [19]
Olson et al.

[11] Patent Number: 5,779,645
[45] Date of Patent: Jul. 14, 1998

[54] SYSTEM AND METHOD FOR WAVEFORM MORPHOLOGY COMPARISON

[75] Inventors: Timothy Scott Olson, San Jose; April Catherine Pixley, Los Altos; Michael O. Williams, Mt. Shasta, all of Calif.

[73] Assignee: Pacesetter, Inc., Sunnyvale, Calif.

[21] Appl. No.: 767,660

[22] Filed: Dec. 17, 1996

[51] Int. Cl.$^6$ ................................................ A61B 5/464
[52] U.S. Cl. .................... 600/518; 600/517; 600/521
[58] Field of Search ................................. 600/509, 510, 600/515, 517, 518, 521

[56] References Cited

U.S. PATENT DOCUMENTS

| | | | |
|---|---|---|---|
| 4,589,420 | 5/1986 | Adams et al. | 128/702 |
| 4,905,708 | 3/1990 | Davies | 128/705 |
| 5,193,550 | 3/1993 | Duffin | 128/697 |
| 5,240,009 | 8/1993 | Williams | 128/702 |
| 5,542,429 | 8/1996 | Feng | 600/515 |
| 5,609,157 | 3/1997 | Panescu et al. | 600/510 |

OTHER PUBLICATIONS

"Separation of Ventricular Tachycardia From Sinus Rhythm Uisng a Practical, Real–time Template Matching Computer System", Greenhut, et al, *PACE*, vol. 15, Nov. Part II 1992, pp. 2146–2153.

"A Comparison of Four New Time–Domain Techniques for Discriminating Monomorphic Ventricular Tachycardia from Sinus Rhythm Uisng Ventricular Waveform Morphology", Throne, et al, *IEEE Transactions on Biomedical Engineering*, vol. 38, No. 6, Jun. 1991, pp. 561–570.

"Template Matching Techniques for Electrophysiologic Signals: A Practical, Real–Time System for Detection of Ventricular Tachycardia", Greenhut, et al, *ISA*, 1992, Paper #92–0116, pp. 37–42.

"Statistical Validation of New Template Matching Methods for Detecting Ventricular Tachycardia", Throne, et al., Computers in Cardiology, Chicago, Illinois, Sep. 23–26, 1990, pp. 103–106.

"Derivative Area Method: A New Technique for Detecting Ventricular Tachycardia", Throne, et al., *Circulation*, Supp. II, vol. 80, No. 4, Oct. 1989, pp. II–658.

"The Bin Area Method: A Computationally Efficient Technique for Analysis of Ventricular and Atrial Intracardiac Electrograms", Throne, et al., *PACE*, vol. 13, Oct. 1990, pp. 1286–1297.

"Area–Of–Difference Methods for Detection of Ventricular Tachycardia Using Morphology" Throne, et al., Computers in Cardiology, Chicago, Illinois, Sep. 23–26, 1990, pp. 569–571.

"Temporal Electrogram Analysis: Algorithm Development", Paul, et al., *PACE*, vol. 13, Dec. 1990, Part II, pp. 1943–1947.

"Automatic Recognition of Ventricular Arrhythmias Using Temporal Electrogram Analysis", Paul, et al., *PACE*, vol. 14, Aug. 1991, pp. 1265–1273.

"Identification of Ventricular Tachycardia with Use of the Morphology of the Endocardial Electrogram", Langberg, et al., *Circulation*, vol. 77, No. 6, Jun. 1988, pp. 1363–1369.

*Primary Examiner*—Jeffrey R. Jastrzab
*Attorney, Agent, or Firm*—Steven M. Mitchell

[57] ABSTRACT

A ventricular tachycardia (VT) complex is distinguished from a sinus tachycardia or a supraventricular tachycardia. A template based on morphology of a normal sinus rhythm is collected. A test signal is compared against the template to determine how closely the test and template signals correspond based on morphology. The comparison is done based on peak information in the template and the test signal. A score is generated to indicate the degree of similarity between the template and the test signal. The peak information is extracted as follows. First, a group of three consecutive peaks having a largest cumulative peak amplitude is located in the template and in the test signal. The polarity, position and area of each peak within the group is then determined. The area of each peak is normalized. The polarities, positions and normalized areas represent the peak information that is used for comparison.

21 Claims, 8 Drawing Sheets

SYSTEM AND METHOD FOR WAVEFORM MORPHOLOGY COMPARISON

BACKGROUND OF THE INVENTION

1. Field of the Invention

The present invention relates generally to comparing waveforms without requiring sample-by-sample comparison. More particularly, the present invention relates to electrogram waveform comparison for discriminating ventricular tachycardia (VT) from sinus tachycardia (ST) and supraventricular tachycardia (SVT).

2. Related Art

In a heart monitoring system, it is often desirable to distinguish between ventricular complexes that are conducted from the atria (i.e., normal complexes) and ventricular complexes that originate in the ventricular myocardium (i.e., abnormal complexes). For example, it is important to be able to distinguish sinus tachycardia (ST) and supraventricular tachycardia (SVT) from ventricular tachycardia (VT). Waveform morphology comparison is normally used to accomplish such discrimination. That is, a test intraventricular electrogram (IVEG) is compared to a template IVEG. The template IVEG is generally taken during a sinus rhythm. If the morphology comparison indicates that there is a ventricular tachycardia, corrective action is taken. For example, implantable cardioverter defibrillators (ICDs) or pacemakers can undertake corrective action when they detect ventricular tachycardia. For a more detailed description of the origin and morphology of these signals, see U.S. Pat. No. 5,340,009 to Williams, entitled "Medical Device with Morphology Discrimination."

A major consideration in developing ICDs is their limited battery power. After implantation, batteries cannot be replaced without surgery and generally the entire ICD is replaced when the batteries are depleted. Thus, it is desirable to conserve battery power. One way to conserve battery power is by reducing the complexity of the signal processing that must be performed by the ICD.

Conventional morphology algorithms compare test and template IVEGs on a point-by-point basis. That is, characteristics about the points in the test IVEG are compared to corresponding points in the template IVEG. Examples of such point-by-point morphology matching processes are disclosed in Greenhut, Saul E. & Steinhaus, Bruce M., *Template Matching Techniques of Electrophysiologic Signals: A Practical Real-Time System for Detection of Ventricular Tachycardia*, Biomedical Scientific Instruments, 1992, Vol. 28, pp. 37–42 (hereinafter "Template Matching Technique") and Greenhut, Saul E. et al., *Separation of Ventricular Tachycardia From Sinus Rhythm Using a Practical, Real-Time Template Matching Computer System*, PACE 1992, 15:2146–2153 (hereinafter "Separation of Ventricular Tachycardia").

Such conventional waveform comparison techniques suffer from several shortcomings. First, waveform alignment is critical to a proper point-by-point comparison. If the test and template signals are not aligned correctly, the result of the waveform comparison can be erroneous. Furthermore, aligning the test and template signals can be a burdensome and time consuming problem.

Second, these conventional point-by-point processing techniques are computationally intensive. For example, such techniques generally require two divide operations. This is illustrated in the equation for the normalized area difference (AND) in the references cited above (see equation (1) on page 39 of "Template Matching Techniques" and equation (1) on page 2148 of "Separation of Ventricular Tachycardia").

Both of these disadvantages result in excess current drain on the battery of an implanted ICD. The excess current drain reduces the life expectancy of the ICD. The reduced life expectancy of the ICD exposes the patient to a greater risk and expense of repeat surgery to replace the device.

Thus, what is needed is an improved method for discriminating ventricular tachycardia (VT) from sinus tachycardia (ST) and supraventricular tachycardia (SVT). Such a method should reduce computational complexity for power savings while at the same time reducing the alignment problem.

SUMMARY OF THE INVENTION

The present invention is directed to distinguishing between a first signal and a second signal on the basis of how well the morphologies of the first and second signals match. The present invention forms a template based on the morphology of a "known" signal. The "known" signal can be, for example, a signal collected during a period where a patient is known to exhibit a normal sinus rhythm. A test signal is compared against the template to determine how closely the signals correspond using their morphology.

In the preferred embodiment, the morphology is represented by a consecutive series of N data samples. From these N data samples, M (e.g., 3) peaks are identified. The positions (i.e., order of occurrence), polarities and normalized areas of the peaks are compared to align the signals and yield a score. A higher score indicates less similarity between the first and second signals.

In the preferred embodiment, the invention is applied to monitoring heart signals to analyze the morphology of an intraventricular electrogram (IVEG) for the purpose of discriminating ventricular tachycardia (VT) from sinus tachycardia (ST) and supra ventricular tachycardia (SVT). A template is generated by analyzing an IVEG depolarization during a sinus rhythm. The polarity and normalized area of the most significant consecutive peaks of the IVEG depolarization are recorded as the template. Each sensed IVEG is matched against the template by comparing the position, polarity and normalized area of the most significant consecutive peaks and summing the differences. The resulting value provides a measure of how similar in morphology the sensed IVEG is to the template IVEG.

Further features and advantages of the invention, as well as the structure and operation of various embodiments of the invention, are described in detail below with reference to the accompanying drawings. In the drawings, like reference numbers generally indicate identical, functionally similar, and/or structurally similar elements. The drawing in which an element first appears is indicated by the digit(s) to the left of the two rightmost digits in the corresponding reference number.

BRIEF DESCRIPTION OF THE FIGURES

The present invention will be described with reference to the accompanying drawings, wherein.

DETAILED DESCRIPTION OF THE PREFERRED EMBODIMENTS

Figure 1:
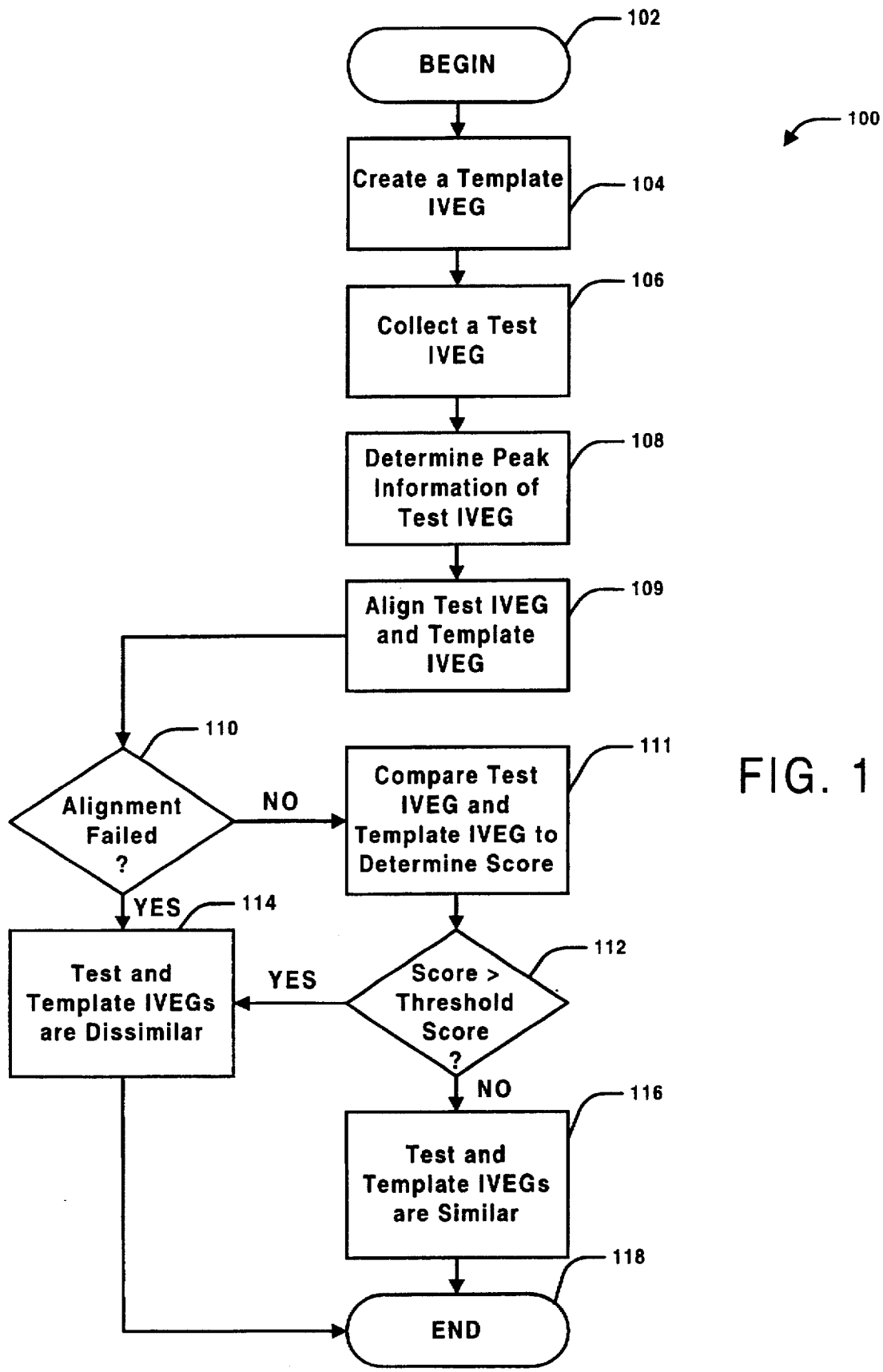
FIG. 1 is a flow chart for a method of morphology comparison of two signals according to a preferred embodiment.

The template matching morphology method of the present invention calculates the difference in the normalized area of each significant peak of a template electrogram (EGM) and a test EGM over a fixed window size of data samples. In addition, the test and template EGMs are not limited to collection from a patient. For example, the test and template EGMs can be computer generated for use, for example, in technique testing.

For purposes of illustrating a preferred embodiment, the invention is described in terms of comparing intraventricular electrograms (IVEGs). It should be understood, however, that this is done for purposes of illustration only. The invention can be used for comparing any cardiac signal whether it is an EGM taken from implanted electrodes or an electrocardiogram (ECG) from surface electrodes or otherwise.

Using a device designed according to the preferred embodiment of the present invention reduces the complexity of waveform morphology diagnosis. As a result, power is conserved and battery life is extended.

A flow chart for a template morphology matching method 100 according to a preferred embodiment of the invention is described with reference to FIG. 1. The beginning of method 100 is indicated in a step 102. In a step 104, a template IVEG is created. The template IVEG is analogous to a standard to which test signals are compared. The template can be generated in a number of well known ways. In the preferred embodiment, the template is generated by simply collecting data points (i.e., digital samples of the IVEG) during a morphology window for a complex in a sinus rhythm. In an alternate embodiment, data is collected over a plurality of morphology windows during which there is a sinus rhythm. After the data is collected, the data is averaged to determine a template. Prior to the averaging however, the data must be aligned. A data alignment mechanism such as described herein can be employed.

As part of the template creation step, the IVEG data is normalized. Normalization accounts for differences in absolute magnitude of the sensed signals that may be affected by variables such as electrode placement, differences in amplifier gain, and the like. Normalization allows the method of the invention to compare the relative magnitudes of the peaks in the IVEG. Normalization of the template IVEG is described in detail below.

The template is generated using morphology information of interest in the signal. In the preferred embodiment, the morphology information selected for comparison is information about M (e.g., 3) consecutive peaks. The peak information includes normalized area, polarity, and position (i.e., order of occurrence) for the M consecutive peaks having the largest sum of peak amplitudes in a collected signal. In the preferred embodiment, the signals are IVEG depolarizations.

After creation of the template IVEG, a test IVEG is collected in a step 106. As discussed below with reference to FIG. 2, the test IVEG is collected over a morphology window 201 in a well known manner.

Next, in a step 108, peak information is identified in the test IVEG. The test and template IVEGs are then aligned in a step 109. Alignment of the test and template IVEG's is tested in a step 110. If alignment failed, then method 100 proceeds to step 114 where the test and template IVEGs are indicated as being dissimilar. If alignment was successful (as indicated at step 110), then method 100 proceeds to step 111.

In step 111, the test and template IVEGs are compared to determine a score. The score represents how well the test and template IVEGs match. The lower the score, the more similar are the test and template IVEGs. The score is compared to a threshold in a step 112. If the score does not exceed the threshold, then the test and template IVEGs are indicated as being similar in a step 116. If the score exceeds the threshold, then the test and template IVEGs are indicated as being dissimilar in step 114.

In the preferred embodiment, the threshold of step 112 is determined by looking at a number of trial runs of a patient in a sinus rhythm and a VT rhythm. The scores are then plotted and viewed. A threshold value is picked that will provide an acceptable (normally very low) probability that a score indicating a VT rhythm is interpreted as a score for a normal sinus rhythm and vice versa.

After either of steps 114 or 116 are executed, method 100 ends as indicated at step 118. Alternatively, method 100 may return to step 106 and repeat. In this manner, method 100 can continuously monitor an input stream of test IVEGs.

As explained in further detail below, this method of the present invention significantly reduces computational complexity. Because the method calculates a normalized area of peaks, there are optimally only three divides required. Importantly, the method of the invention improves over conventional methods by not requiring two divides per sample point. Moreover, the alignment problem is solved by aligning on the basis of morphology (i.e., peak polarity and peak amplitude), rather than corresponding data points (samples).

The steps of method 100 are now explained in further detail with reference to FIGS. 2-8.

Figure 2:
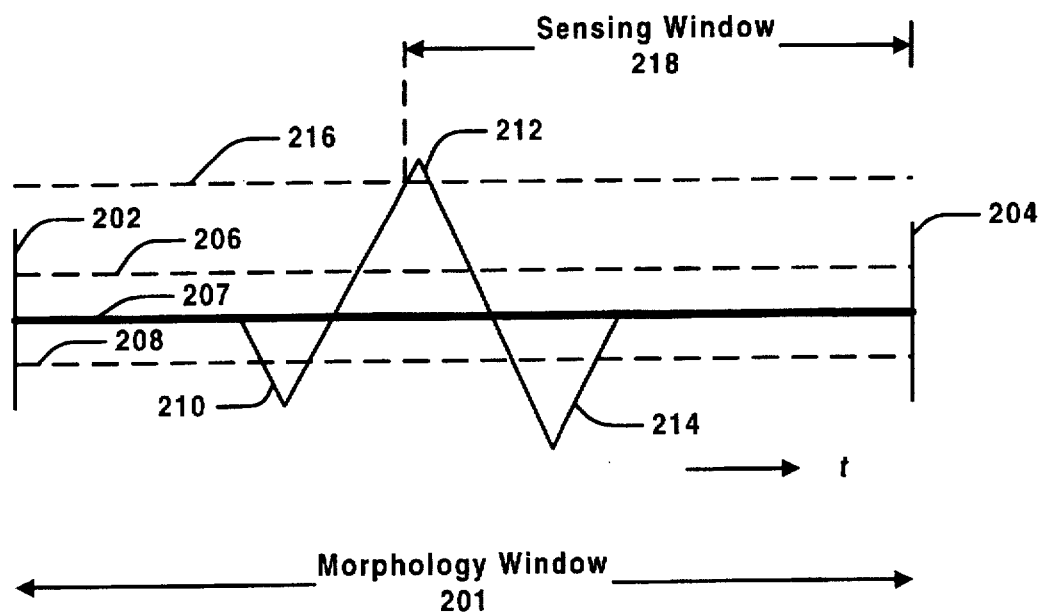
FIG. 2 is a graphic representation of an IVEG collected during a morphology window.

FIG. 2 illustrates a graphical representation of a single IVEG depolarization to be collected in step 106. The test IVEG is collected and sampled during a morphology window 201 in a well known manner. Morphology window 201 begins at a time 202 and ends at a time 204. During the morphology window 201, N data samples of the IVEG depolarization are taken.

Referring still to FIG. 2, step 108 of determining peak information of the test IVEG is described. A peak is defined to begin with the data sample that is greater than (in absolute magnitude) or equal to a fixed threshold 206 or 208 (in absolute magnitude). A peak is defined to end with the data sample that crosses the baseline 207. Three peaks 210, 212 and 214 are illustrated. Peak 212 is the dominant peak, peak 214 is the second dominant peak, and peak 210 is the third dominant peak. The peaks must be consecutive.

FIG. 2 also illustrates a sensing window 218. Sensing widow 218, also known as the sense refractory period, begins when a peak rises above a sensing threshold 216. The end of the sensing window 218 corresponds to the end of morphology window 201.

As illustrated in FIG. 2, peaks may be collected both before and after sensing window 218 begins. In the present invention, M (e.g., 3) peaks having the largest sum of peak amplitudes are used to analyze the waveform morphology. While three peaks are preferred in the present implementation of the invention, a person skilled in the art will recognize that a different number of peaks (e.g., 2, 4 or more) may be used.

Figure 3:
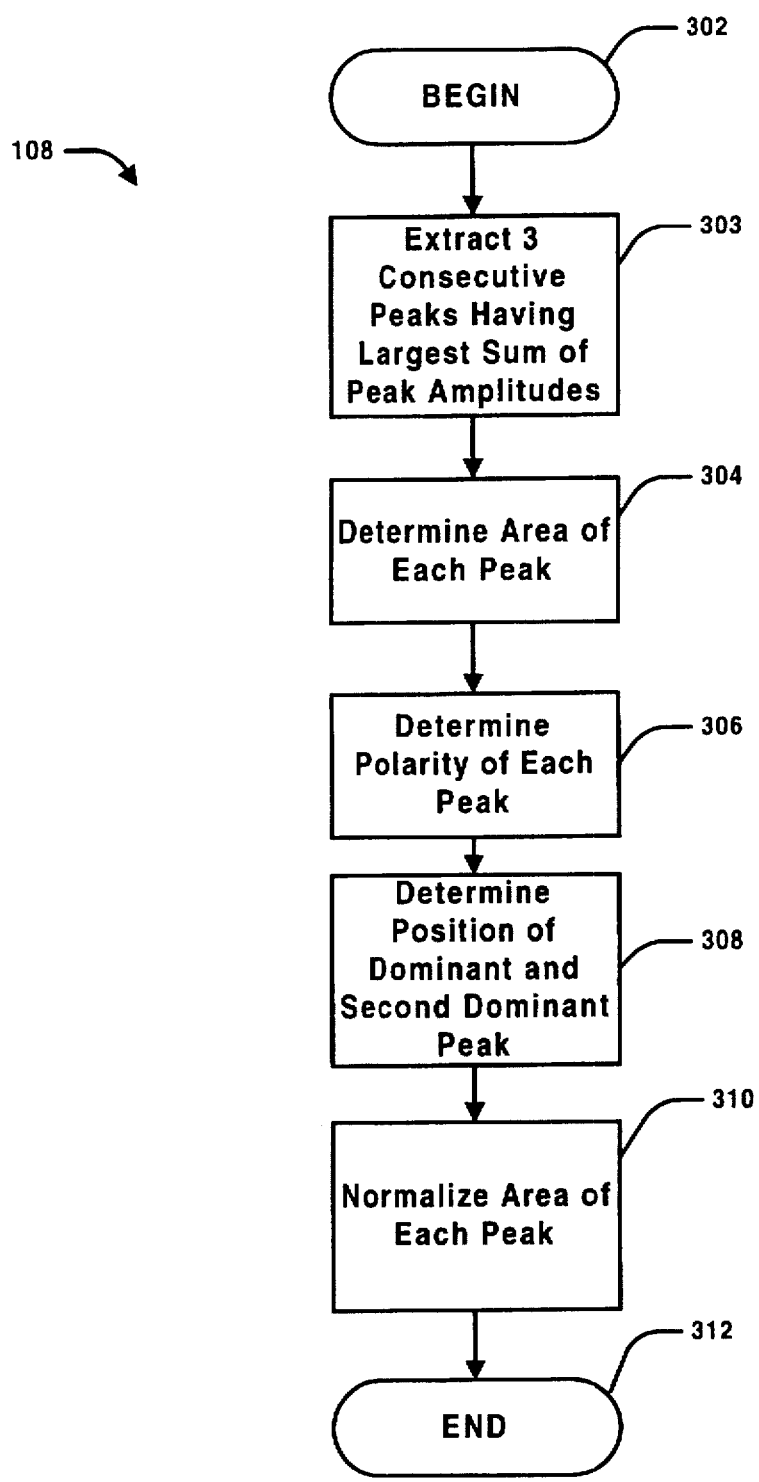
FIG. 3 is a flow chart for determining peak information of interest according to the preferred embodiment.

FIG. 3 illustrates in further detail step 108 (see FIG. 1) of determining peak information for the test IVEG. The peak information includes the normalized area of each peak, the polarity of each peak, and the positions (not in absolute time, but in order of occurrence) of the dominant and second dominant peaks in the test IVEG.

When performing step 108, the method of peak determination begins in a step 302. In a step 303, the three consecutive peaks with the largest sum of peak amplitudes are extracted. Next, in a step 304, the area is calculated for each of the three peaks selected in step 303. The area is essentially the size of the peak. In the preferred embodiment, the area is simply the arithmetic sum of the data points (amplitudes) in the peak. It would be apparent to those skilled in the art that other methods for calculating area can be used.

After determining the area for each of the three peaks selected in step 303, the method executes step 306. In step 306, the polarity of each of the peaks selected in step 303 is determined. Polarity refers to whether a peak is greater than zero (positive) or less than zero (negative). For example, peak 212 has positive polarity, whereas peaks 210 and 214 have negative polarities.

After determining the polarity for each of the peaks, the positions of the most dominant and second most dominant peaks in the three-peak set are determined in a step 308. Note that, in the preferred embodiment, peak dominance is measured by peak amplitude, rather than by peak area. Also note that this position determination refers to a relative position or order of occurrence (e.g., third dominant peak in a first position, dominant peak in a second position, and second dominant peak in a third position as for FIG. 2) rather than an absolute position (e.g., dominant peak at 63 msec, second peak at 71 msec, etc.) within the morphology window.

After determining the relevant positions, the area of each peak is normalized in a step 310. In the preferred embodiment the normalization proceeds according to Equation (1) for each peak in the 3-peak set selected:

$$NormAreaPeak_x = \left| \frac{AreaPeak_x}{|AreaPeak_1| + |AreaPeak_2| + |AreaPeak_3|} \right| \quad \text{Equation (1)}$$

In an alternate preferred embodiment, the normalized area of each peak is calculated according to Equation (2).

$$NormAreaPeak_x = \left| \frac{AreaPeak_x}{|PeakWithMaxArea|} \right| \quad \text{Equation (2)}$$

The subscript x in Equations (1) and (2) indicates that the calculation is done for each peak selected in step 303. After normalization, the method ends at step 312 to complete the determination of peak information for the test IVEG.

Step 109 of FIG. 1 represents alignment of the test and template IVEGs. This step is detailed in FIG. 4. The method of FIG. 4 begins in a step 402. In a step 403, an attempt is made to match the polarity of a dominant peak in the template IVEG with the polarity of a dominant peak in the test IVEG. Step 403 is described in further detail below with reference to FIG. 5.

A step 404 determines whether the peak polarity matching of step 403 was successful. If decision step 404 determines that peak polarities do not match, then step 407 determines that the alignment failed and the method continues to step 408. In step 408, the method of step 109 ends and returns to the method of FIG. 1. If, on the other hand, step 404 determines that the peak polarities do match, then the method continues to step 405.

Step 405 determines whether the peaks with matching polarities in the test and template IVEGs correspond to one another in position. Peaks that correspond are peaks having the same sequential position in a particular IVEG. For example, if the peak positions are numbered from one to three, the peak in position one in the test IVEG corresponds to the peak in position one in the template IVEG. If step 405 indicates that the peaks in the test and template IVEGs correspond to one another in position, then the method continues to step 408. In step 408, the method of step 109 ends and returns to the method of FIG. 1.

If, on the other hand, decision step 405 determines that the peaks in the test and template IVEGs do not correspond in position, then the method of step 109 continues with step 406. In step 406, the method attempts to align the peaks by shifting the dominant peak of the test IVEG to the right or the left. The effect of this shifting is to drop a non-dominant peak off of one side of the three peak group and to add another peak to the other side of the three peak group. This will align the peaks between the test and template IVEGs. Step 406 is described in detail below with reference to FIG. 6.

Figure 4:
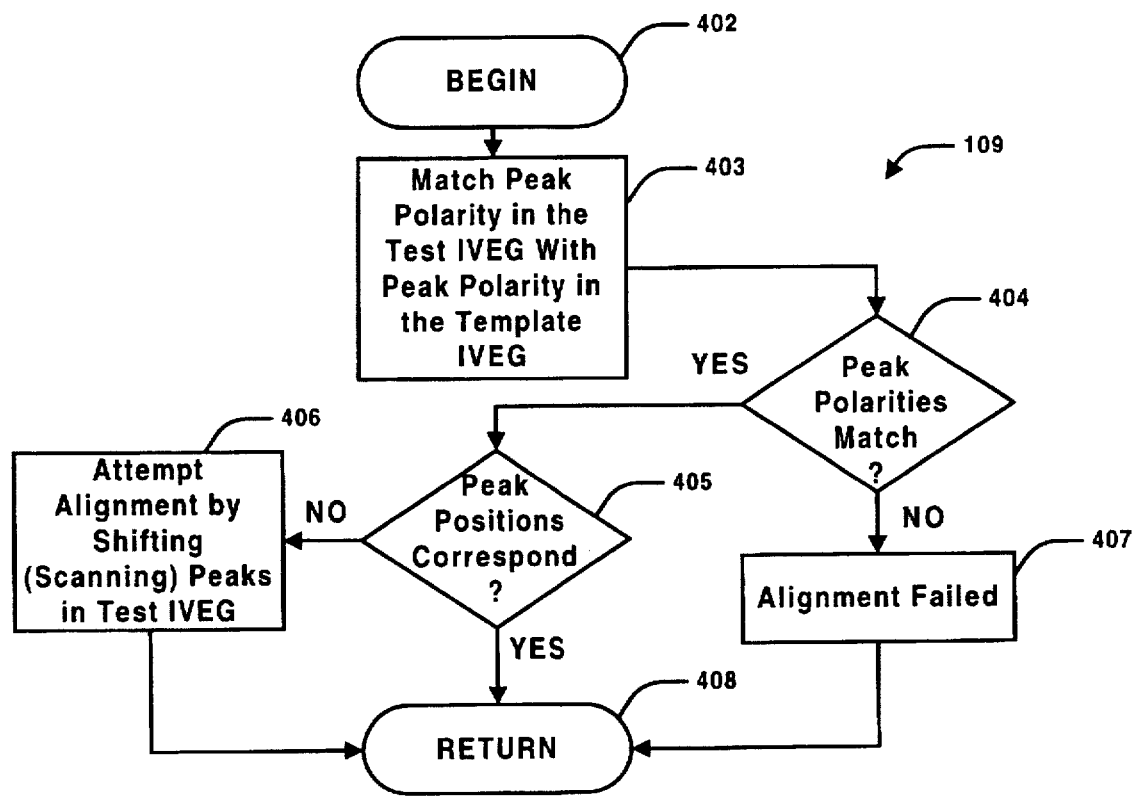
FIG. 4 is a flow chart for aligning a test and a template IVEG according to a preferred embodiment.
Figure 5:
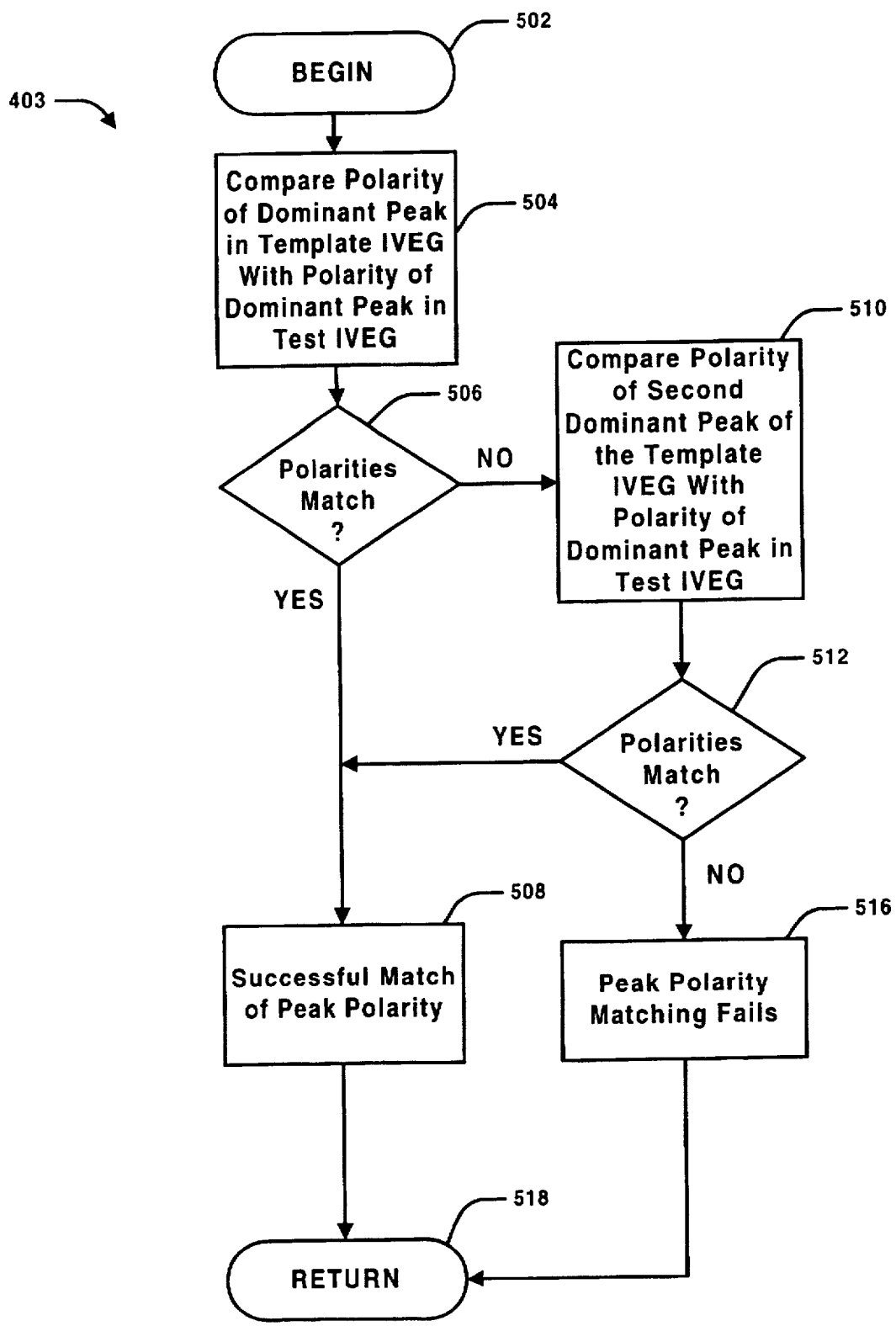
FIG. 5 is a flow chart for determining whether peaks match according to a preferred embodiment.

Step 403 of matching peak polarities in the test IVEG with peaks in the template IVEG is now described in further detail with reference to FIG. 5. The method begins in a step 502. In step 504, the polarity of the dominant peak of the template IVEG is compared to the polarity of the dominant peak of the test IVEG. The result of the comparison is checked in a step 506. If the polarities match, then a successful match is indicated at step 508. The method then ends and returns to the method of FIG. 4, as indicated at step 518.

If, at step 506, it is determined that the polarities of the dominant peaks do not match between the test and template IVEGs, then the method continues to step 510. In step 510, the method compares the polarity of the second dominant peak of the template IVEG with the dominant peak of the test IVEG. The method checks the result of the comparison in decision step 512. If the polarities match, then a successful match in indicated at step 508. The method then continues to step 518. If matching is done on the basis of the "second dominant" peak of the template IVEG, this second dominant peak will be called the "dominant" peak of the template IVEG for the remainder of the method. This is done for ease of explanation.

If, at step 512, it is determined that the polarities of the second dominant peak of the template IVEG and the dominant peak of the test IVEG do not match, then the method continues to step 516. In step 516, the method indicates that the peak polarity matching has failed. The method then continues to step 518. If peak polarity matching has failed, then alignment of the test and template IVEGs is not possible. This causes a failure of alignment in step 407 of FIG. 4.

Step 406 of shifting peaks in the test IVEG is now described in greater detail. Step 406 is only reached if the initial peak polarity matching of step 403 (see FIG. 4) is successful, but the positions of the dominant peaks do not correspond (recall that the "second dominant" peak of the template IVEG is considered the "dominant" peak if matching is done on that basis). Step 406 attempts to make the peaks of the test IVEG correspond in position to the peaks of the template IVEG.

Figure 6:
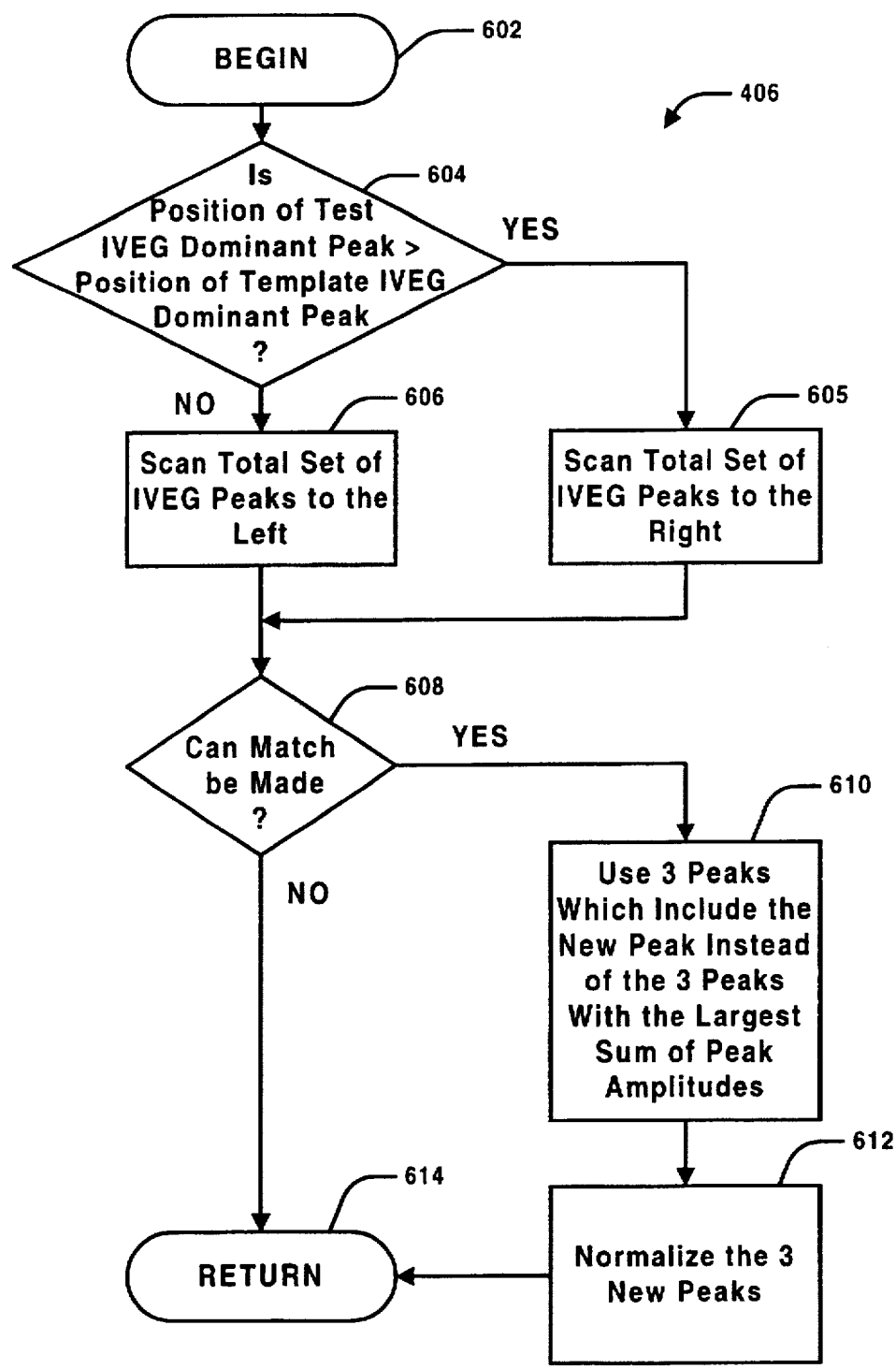
FIG. 6 is a flow chart for determining whether peak positions match and for correcting mismatch according to a preferred embodiment.

Step 406 is described in detail with reference to FIG. 6. The method of FIG. 6 begins at step 602. In step 604, it is determined whether the position of the dominant peak in the test IVEG is greater than the position of the dominant peak in the template IVEG (recall that the "second dominant" peak of the template IVEG is considered the "dominant" peak if matching is done on that basis). If the test dominant peak has a greater position than the template dominant peak (e.g., test peak at position #2 > template peak at position #1), then it may be possible to align the peaks by shifting the test peaks to the left. A shift does not actually occur. Rather, the test IVEG is inspected or scanned to the right side of the dominant peak. If a new peak is found that matches (in polarity and position) the peak to the right of the dominant peak of the template IVEG, then that new peak is added to the three peak group and the peak that previously occurred to the left of the dominant peak is dropped. Thus, a new group of test peaks is formed. This is indicated by step 605.

If the test dominant peak has a lesser position than the template dominant peak (e.g., test peak at position #2 < template peak at position #3), then it may be possible to align the peaks by shifting the test peaks to the right. As explained above, a shift does not actually occur. Rather, the test IVEG is inspected or scanned to the left side of the dominant peak. If a new peak is found that matches (in polarity and position) the peak to the left of the dominant peak of the template IVEG, then that new peak is added to the three peak group and the peak that previously occurred to the right of the dominant peak is dropped. Thus, a new group of test peaks is formed. This is indicated by step 606.

Note that in performing this searching or scanning of steps 605 and 606, the three peaks that are chosen from the test IVEG must be consecutive. Thus, if a mismatching peak occurs on the left side of the dominant peak of the test IVEG, then only the right side can be checked for a matching peak. Similarly, if a mismatching peak occurs on the right side of the dominant peak of the test IVEG, then only the left side can be checked for a matching peak. If a new peak is found in either of steps 605 or 606, the new peak is added to the test IVEG and the mismatched peak is dropped from the test IVEG, as described above, to form a new 3 peak group for the test IVEG.

After scanning left or right, the method continues in decision step 608 to determine whether the scanning was successful in matching peaks. If no match can be made, the method proceeds to step 614 where the method ends and returns to the method of FIG. 4. If a new peak was found so that the polarities of the three new peaks in the test IVEG match the corresponding peaks in the template IVEG, then the method continues in step 610.

In step 610, the method selects the three new peaks of the test IVEG for comparison to the template IVEG in step 111 (see FIG. 1). The method then continues to step 612. In step 612, the three new peaks of the test IVEG are normalized using either of Equation (1) or Equation (2) above. The method then continues with step 614. In step 614, the method returns to FIG. 4, and continues in step 408.

Figures 7A, 7B:
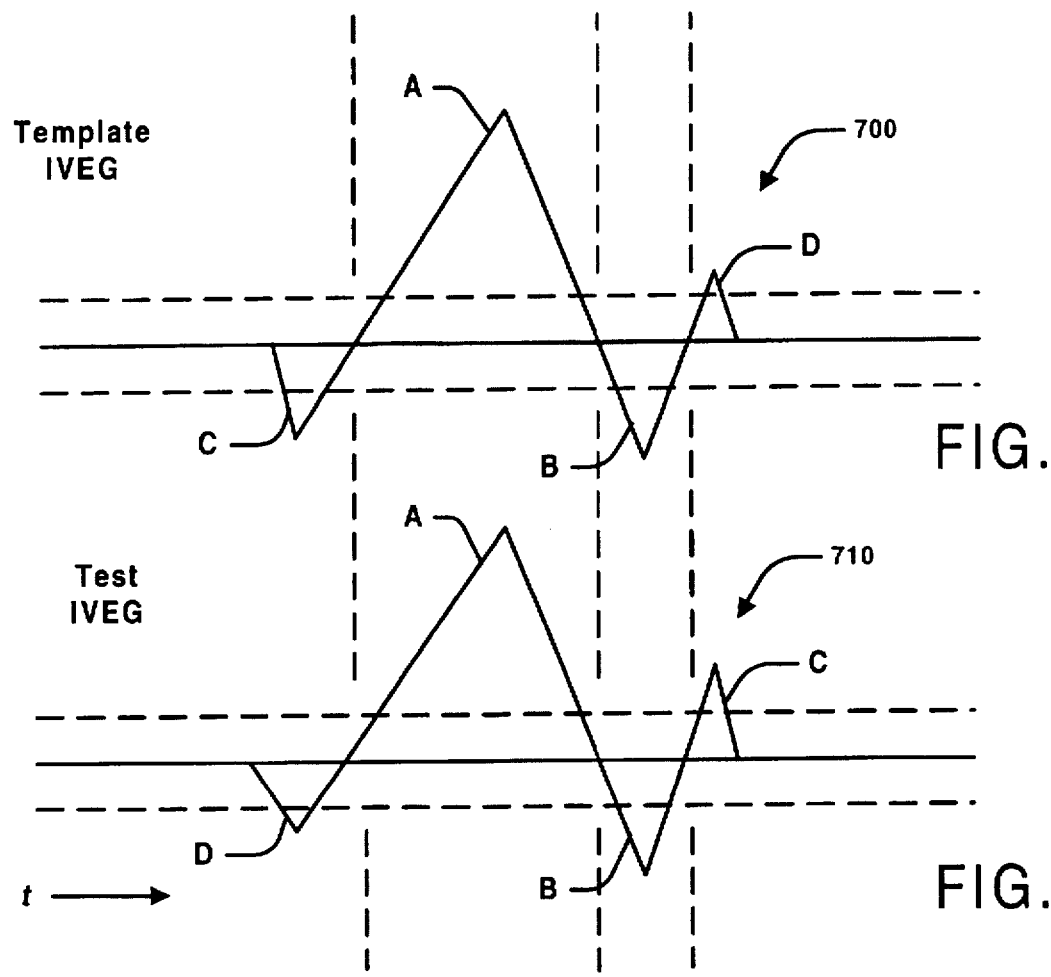
FIGS. 7A and 7B illustrate example mismatch correction using the flow chart of FIG. 6.

FIGS. 7A and 7B. FIG. 7A illustrates a template IVEG 700 and FIG. 7B illustrates a test IVEG 710. Dashed vertical lines have been drawn over the two IVEGs to show the correspondence therebetween. Note that template IVEG 700 has a dominant peak A, a second dominant peak B, a third dominant peak C and a fourth dominant peak D. The three dominant peaks occur in the order of: C-A-B. Note that test IVEG 710 also has a dominant peak A, a second dominant peak B, a third dominant peak C and a fourth dominant peak D. However, note that the three dominant peaks occur in a different order with respect to the peaks of template IVEG 700. The three dominant peaks of the test IVEG occur in the order of A-B-C. Thus, step 405 of FIG. 4, would return an indication that the peaks do not correspond in position. This non-correspondence is illustrated in the following table:

| IVEG | Position #1 | Position #2 | Position #3 |
| --- | --- | --- | --- |
| Template | C | A | B |
| Test | A | B | C |

Correction of this misalignment according to step 406 of FIG. 4 would proceed as detailed in FIG. 6 as follows. Because peak A (i.e., the dominant peak) of test IVEG 710 occurs first in the three peak group, it is in position #1. However, peak A of template IVEG 700 occurs after peak C. Thus, peak A of template IVEG 700 is in position #2. Step 604 determines whether the test peak A has a greater position than template peak A (i.e., is test peak A at position #1 > template peak A at position #2). In this case, the test peak position is not greater than the template peak position. Therefore, the method proceeds to step 606 where the test IVEG is shifted right (i.e., the IVEG is inspected to the left side of the current three peak group in an attempt to find the next consecutive peak). This operation will locate fourth dominant peak D.

Note that peak D matches (in polarity and position) (see step 608) peak C of the template IVEG. Therefore, peak D is added to the three peak group and peak C is dropped from the three peak group for the test IVEG. This shift operation results in alignment of the peaks between the test IVEG and template IVEG as illustrated in the following table:

| IVEG | Position #1 | Position #2 | Position #3 |
| --- | --- | --- | --- |
| Template | C | A | B |
| Test | D | A | B |

Note that peak D is taken as the third dominant peak of the test IVEG even though it is really fourth largest in amplitude. This correction to the three peak group of the test IVEG results in all peaks of the test IVEG having matching peaks of the template IVEG.

In the preferred embodiment, the three new peaks of the test IVEG may then be normalized (as indicated in step 612), and a score calculated in accordance with step 111 of FIG. 1. The following equations can be used to calculate a score: where:

UnmatchedTemplatePeaks = Normalized Areas of the unmatching template peaks

UnmatchedTestPeaks = Normalized Areas of the unmatching test peaks $$\text{score} = \Sigma |\text{UnmatchedTemplatePeaks}| + \quad \text{Equation (3)}$$
$$\Sigma |\text{UnmatchedTestPeaks}| +$$
$$\Sigma |\text{MatchedTemplatePeaks} - \text{MatchedTestPeaks}|$$

MatchedTemplatePeaks = Normalized Areas of the matching template peaks

MatchedTestPeaks = Normalized Areas of the matching test peaks

In the case where the alignment position of the three consecutive peaks is the same for both the template and the test IVEGs (i.e., the test and template complexes match), Equation (3) reduces to Equation (4):

$$\text{Score} = |\text{TemplatePeak}_1 - \text{TestPeak}_1| + \quad \text{Equation (4)}$$
$$|\text{TemplatePeak}_2 - \text{TestPeak}_2| +$$
$$|\text{TemplatePeak}_3 - \text{TestPeak}_3|$$

where:

$\text{TemplatePeak}_1$ = Normalized Area of dominant template peak $\text{TestPeak}_1$ = Normalized Area of dominant test peak $\text{TemplatePeak}_2$ = Normalized Area of second dominant template peak $\text{TestPeak}_2$ = Normalized Area of second dominant test peak $\text{TemplatePeak}_3$ = Normalized Area of third dominant template peak $\text{TeatPeak}_3$ = Normalized Area of third dominant test peak Thus, in the preferred embodiment the method uses Equation (3) when some peaks have no match in the test and template IVEGs and Equation (4) when a match is found between all three peaks of the test and template IVEGs. If desired, however, Equation (3) may be used in all cases.

As can be seen from Equations (3) and (4), the score indicates the relative similarity between the test and template IVEGS. In the preferred embodiment, a smaller score indicates relative similarity, while a larger score indicates that the two IVEGs are dissimilar.

Figure 8:
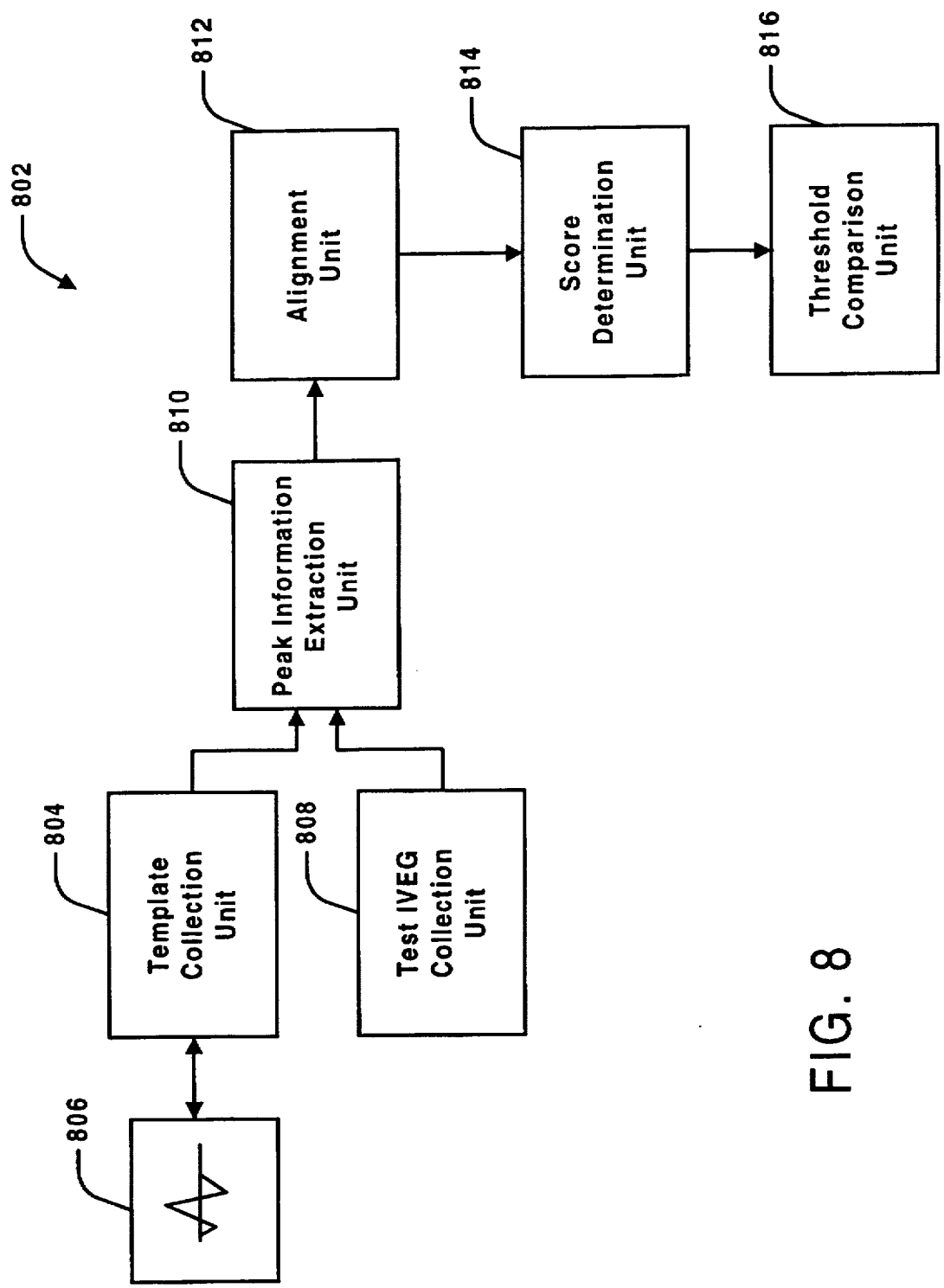
FIG. 8 is a system for morphology comparison of two signals according to a preferred embodiment.

FIG. 8 illustrates a system 802 according to a preferred embodiment of the present invention. Although applicable to signals in general, the system illustrated in FIG. 8 is directed toward the preferred embodiment of IVEGs in an implantable cardiac pacing or defibrillation device. The system contains a template collection unit 804, a test IVEG collection unit 808, a peak information extraction unit 810, an alignment unit 812, a score determination unit 814, and a threshold comparison unit 816. In addition, the system includes a template storage area 806.

The template collection unit 804 creates a template as described above. In the preferred embodiment the template so created is stored in a template storage area 806. Thus, a template need not be created each time a test IVEG is to be compared to a template. Rather a template can be retrieved from the template storage area 806 and passed to that template collection unit 804 for subsequent processing in the system.

The test IVEG collection unit 808 collects a test IVEG for determination of whether the test IVEG is a sinus or VT complex. The test IVEG collection unit 808 collects a test IVEG during a sense refractory period in a well-known manner. The test IVEG collection unit 808 and template collection unit 804 are coupled to a peak information extraction unit 810.

The peak information extraction unit 810 extracts peak information of interest from both the template and test IVEGs for the comparison phase of the present invention. As explained above, the peak information of interest according to a preferred embodiment are the normalized area, polarity, and position of each of the three consecutive peaks having the largest sum of peak amplitudes in a collected signal. In addition, the peak information extraction unit 810 normalizes the areas of the 3 consecutive peaks. The peak information extraction unit 810 is coupled to an alignment unit 812.

The alignment unit 812 determines whether the template and test IVEGs are aligned as described above. The alignment unit 812 is coupled to a score determination unit 814. The alignment unit 812 transmits an indication of whether the test and template signals match to the score determination unit 814.

The score determination unit 814 receives the match indication from the alignment unit 812. The score determination unit calculates a score using Equation (3) or Equation (4), as described above. Whether the system uses Equation (3) or Equation (4), depends on the received match indication. If the received match indication indicates no match, the system uses Equation (3). If on the other hand, the received match indication indicates a match, the system uses Equation (4). The score determination unit is coupled to a threshold comparison unit 816. Note that the system, if desired, could use Equation (3) regardless of whether a match is indicated.

The threshold comparison unit 816 compares the score to a threshold (described above). If the score is greater than the threshold, then the test and template signals are dissimilar. However, if the score is less than the threshold, the test and template signals are similar to one another.

Figure 9:
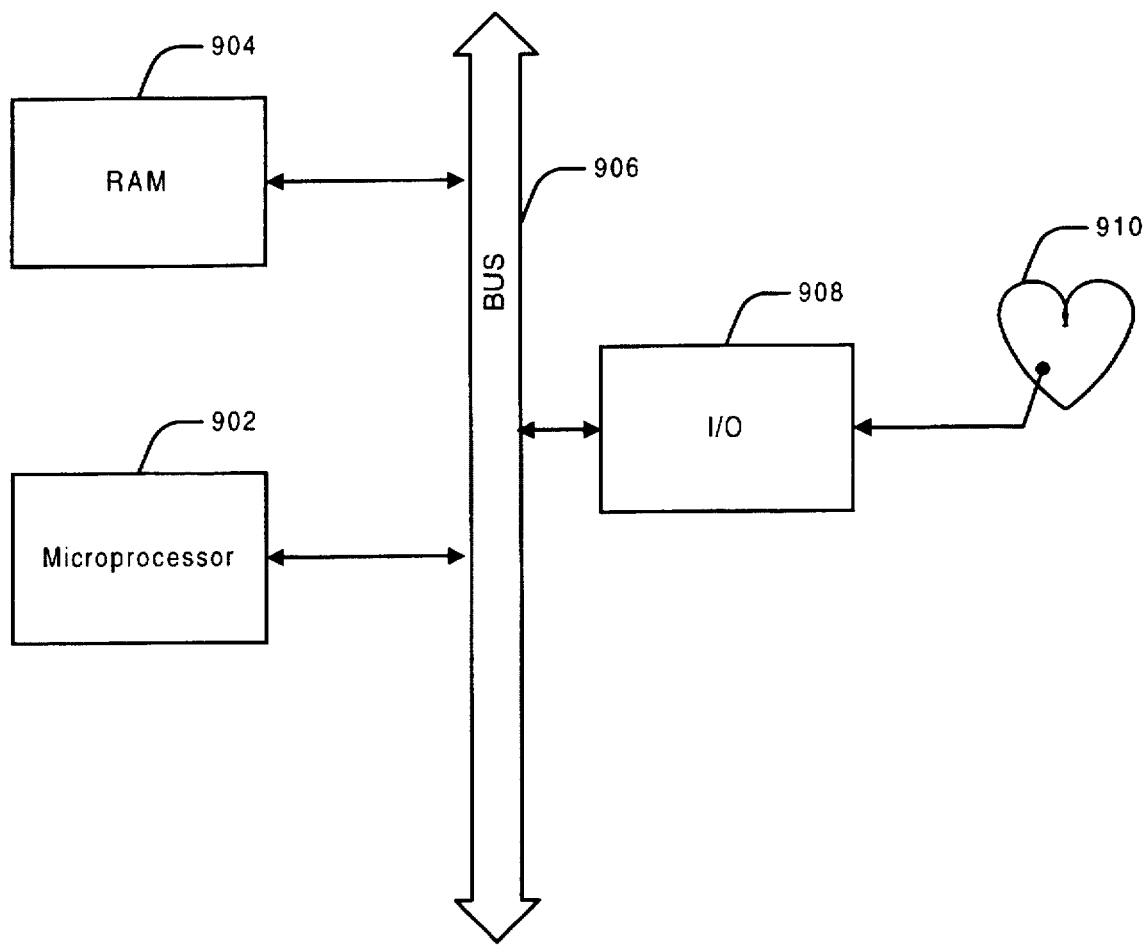
FIG. 9 is a schematic representation of a preferred implementation of the system for morphology comparison of two signals in FIG. 8.

FIG. 9 illustrates the preferred embodiment for the system described in FIG. 8. The preferred embodiment includes a microprocessor 902, a random access memory (RAM) 904, an input/output (I/O) unit 908, and a bus 906. The functionality of system 802 is implemented in software in microprocessor 902. Bus 906 provides for communication between RAM 904, microprocessor 902 and input/output unit 908. I/O unit 908 is also coupled to a patient's heart 910 in a well known manner to collect the template and test IVEGs.

In FIG. 9, microprocessor 902 instructs I/O unit 908 to collect a template IVEG. I/O unit 908 collects the template IVEG in a well-known manner. I/O unit 908 stores the template IVEG in RAM 904 over bus 906. Microprocessor 902 extracts peak information from the template IVEG and stores the peak information in RAM 904. The original template IVEG can be discarded. At a later time, microprocessor 902 instructs I/O unit 908 to collect a test IVEG. The test IVEG is stored in RAM 904 over bus 906. Microprocessor 902 extracts peak information from the test IVEG and stores the information in RAM 904. The original test IVEG can then be discarded. After obtaining the peak information from the test IVEG, microprocessor 902 performs the alignment of alignment unit 812 and determines the score as explained with reference to score determination unit 814. Microprocessor 902 then performs a threshold comparison test as explained with reference to threshold comparison unit 816 to determine whether the test and template IVEGs match.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A method for comparing a test electrogram to a template electrogram, comprising the steps of:

(a) collecting a template electrogram;

(b) collecting a test electrogram;

(c) locating a group of three consecutive peaks having a largest cumulative peak amplitude in said template electrogram and extracting template peak information from that portion of said template electrogram;

(d) locating a group of three consecutive peaks having a largest cumulative peak amplitude in said test electrogram and extracting test peak information from that portion of said test electrogram;

(e) comparing polarities and positions of said test peak information with polarities and positions of said template peak information to align said test electrogram with said template electrogram; and (f) comparing said test peak information with said template peak information to generate a score indicative of similarity between said template electrogram and said test electrogram to thereby provide an indication of whether said test and template electrograms originate from a same region of a patient's heart.

2. The method of claim 1, wherein said electrograms are intraventricular electrograms and wherein step (a) comprises the steps of:

collecting a plurality of intraventricular electrograms during a morphology window corresponding to a sinus rhythm; and averaging said plurality of intraventricular electrograms to generate said template intraventricular electrogram.

3. The method of claim 2, wherein step (b) comprises the step of:

collecting a test intraventricular electrogram during a morphology window.

4. The method of claim 3, wherein each of said steps (c) and (d) further comprise the following steps:

determining a polarity of each peak within said group;

determining a position of each peak within said group; and normalizing the area of each peak in said group, wherein said polarities, said positions and said normalized areas represent said extracted peak information.

5. The method of claim 4, wherein step (e) comprises the steps of:

comparing the polarity of a dominant test peak to the polarity of a dominant template peak;

if the polarity of said dominant test peak matches the polarity of said dominant template peak, then aligning said template intraventricular electrogram with said test intraventricular electrogram on the basis of said dominant peaks;

if the polarity of said dominant test peak does not match the polarity of said dominant template peak, then comparing the polarity of said dominant test peak to the polarity of a second dominant template peak;

if the polarity of said dominant test peak matches the polarity of said second dominant template peak, then aligning said template intraventricular electrogram with said test intraventricular electrogram on the basis of said dominant test peak and said second dominant template peak; and if the polarity of said dominant test peak does not match the polarity of either said dominant template peak or said second dominant template peak, then indicating that the test and template intraventricular electrograms could not be aligned.

6. The method of claim 5, wherein said aligning steps comprise the steps of:

determining whether positions of said test peaks correspond to positions of said template peaks; and if said positions of said test peaks do not correspond to positions of said template peaks, then scanning said test intraventricular electrogram for another peak with which a match can be made.

7. The method of claim 6, wherein step (f) comprises the steps of:

if peaks in said template intraventricular electrogram and said test intraventricular electrogram do not match in position and polarity, then calculating said score as the sum of the magnitudes of the areas of unmatched template peaks, the areas of unmatched test peaks, and the difference between the areas of any matched template and test peaks; and if peaks in said template intraventricular electrogram and said test intraventricular electrogram all match in position and polarity, then calculating said score as the sum of the magnitudes of the differences between the areas of the matched peaks.

8. The method of claim 1, wherein each of said steps (c) and (d) further comprise the following steps:

determining a polarity of each peak within said group;

determining a position of each peak within said group; and normalizing the area of each peak in said group, wherein said polarities, said positions and said normalized areas represent said extracted peak information.

9. The method of claim 8, wherein said normalization step comprises the step of:

normalizing each peak with respect to the sum of the areas of each of said 3 consecutive peaks.

10. The method of claim 8, wherein said normalization step comprises the step of:

normalizing each peak with respect to a peak having the largest area of said three consecutive peaks.

11. The method of claim 1, wherein step (e) comprises the steps of:

comparing the polarity of a dominant test peak to the polarity of a dominant template peak;

if the polarity of said dominant test peak matches the polarity of said dominant template peak, then aligning said template electrogram with said test electrogram on the basis of said dominant peaks;

if the polarity of said dominant test peak does not match the polarity of said dominant template peak, then comparing the polarity of said dominant test peak to the polarity of said second dominant template peak;

if the polarity of said dominant test peak matches the polarity of said second dominant template peak, then aligning said template electrogram with said test electrogram on the basis of said dominant test peak and said second dominant template peak; and if the polarity of said dominant test peak does not match the polarity of either said dominant template peak or said second dominant template peak, then indicating that the test and template electrograms could not be aligned.

12. The method of claim 11, wherein said aligning steps comprise the steps of:

determining whether positions of said test peaks correspond to positions of said template peaks; and if said positions of said test peaks do not correspond to positions of said template peaks, then scanning said test electrogram for another peak with which a match can be made.

13. A method for comparing a test electrogram to a template electrogram, comprising the steps of:

(a) collecting a template electrogram;

(b) collecting a test electrogram;

(c) extracting template peak information from said template electrogram;

(d) extracting test peak information from said test electrogram;

(e) comparing polarities and positions of said test peak information with polarities and positions of said template peak information to align said test electrogram with said template electrogram;

(f) comparing said test peak information with said template peak information to generate a score indicative of similarity between said template electrogram and said test electrogram;

(g) if in step (e) peaks in said template electrogram and said test electrogram do not match in position and polarity, then in step (f) calculating said score as the sum of the magnitudes of the areas of unmatched template peaks, the areas of unmatched test peaks, and the difference between the areas of any matched template and test peaks; and (h) if in step (e) peaks in said template electrogram and said test electrogram all match in position and polarity, then in step (f) calculating said score as the sum of the magnitudes of the differences between the areas of the matched peaks.

14. An apparatus for comparing a test electrogram to a template electrogram, comprising:

(a) collection means for collecting and storing a template electrogram and a test electrogram;

(b) peak extraction means for extracting template peak information from said template electrogram and for extracting test peak information from said test electrogram) said extraction means comprising means for locating a group of three consecutive peaks having a largest cumulative area in said electrogram, means for determining a polarity of each peak within said group, means for determining a position of each peak within said group, and means for normalizing the area of each peak in said group, wherein said polarities, said positions and said normalized areas represent said extracted peak information;

(c) comparison means for comparing polarities and positions of said test peak information with polarities and positions of said template peak information to align said test electrogram with said template electrogram; and (d) score means for comparing said test peak information with said template peak information to generate a score indicative of similarity between said template electrogram and said test electrogram to thereby provide an indication of whether said test and template electrograms originate from a same region of a patient's heart.

15. The apparatus of claim 14, wherein said comparison means comprises:

means for comparing the polarity of a dominant test peak to the polarity of a dominant template peak;

means for aligning said template electrogram with said test electrogram on the basis of said dominant peaks if the polarity of said dominant test peak matches the polarity of said dominant template peak;

means for comparing the polarity of said dominant test peak to the polarity of said second dominant template peak if the polarity of said dominant test peak does not match the polarity of said dominant template peak;

means for aligning said template electrogram with said test electrogram on the basis of said dominant test peak and said second dominant template peak if the polarity of said dominant test peak matches the polarity of said second dominant template peak; and means for indicating that the test and template electrograms could not be aligned if the polarity of said dominant test peak does not match the polarity of either said dominant template peak or said second dominant template peak.

16. The apparatus of claim 15, wherein said means for aligning comprises:

means for determining whether positions of said test peaks correspond to positions of said template peaks; and means for scanning said test electrogram for another peak with which a match can be made if said positions of said test peaks do not correspond to positions of said template peaks.

17. The apparatus of claim 16, wherein said score means comprises:

means for calculating said score as the sum of the magnitudes of the areas of unmatched template peaks, the areas of unmatched test peaks, and the difference between the areas of any matched template and test peaks if peaks in said template electrogram and said test electrogram do not match in position and polarity; and means for calculating said score as the sum of the magnitudes of the differences between the areas of the matched peaks if peaks in said template electrogram and said test electrogram all match in position and polarity.

18. A method for distinguishing between a ventricular tachycardia complex and a sinus tachycardia or supra ventricular tachycardia complex, comprising the steps of:

(a) collecting a template intraventricular electrogram and a test intraventricular electrogram;

(b) for each of said intraventricular electrograms, (1) locating a group of three consecutive peaks having a largest cumulative area, (2) determining a polarity and a position of each peak within said group, and (3) normalizing the area of each peak in said group, wherein said polarities, said positions and said normalized areas represent extracted peak information;

(c) comparing polarities and positions of said extracted peak information for said test intraventricular electrogram with polarities and positions of said extracted information for said template intraventricular electrogram to align said test intraventricular electrogram with said template intraventricular electrogram; and (d) comparing said extracted peak information for said test intraventricular electrogram with said extracted information for said template intraventricular electrogram to generate a score indicative of similarity between said template intraventricular electrogram and said test intraventricular electrogram.

19. The method of claim 18, wherein step (c) comprises the steps of:

comparing the polarity of a dominant test peak to the polarity of a dominant template peak;

if the polarity of said dominant test peak matches the polarity of said dominant template peak, then aligning said template intraventricular electrogram with said test intraventricular electrogram on the basis of said dominant peaks;

if the polarity of said dominant test peak does not match the polarity of said dominant template peak, then comparing the polarity of said dominant test peak to the polarity of said second dominant template peak;

if the polarity of said dominant test peak matches the polarity of said second dominant template peak, then aligning said template intraventricular electrogram with said test intraventricular electrogram on the basis of said dominant test peak and said second dominant template peak; and if the polarity of said dominant test peak does not match the polarity of either said dominant template peak or said second dominant template peak, then indicating that the test and template intraventricular electrograms could not be aligned.

20. The method of claim 19, wherein said aligning steps comprise the steps of:

determining whether positions of said test peaks correspond to positions of said template peaks; and if said positions of said test peaks do not correspond to positions of said template peaks, then scanning said test intraventricular electrogram for another peak with which a match can be made.

21. The method of claim 20, wherein step (d) comprises the steps of:

if peaks in said template intraventricular electrogram and said test intraventricular electrogram do not match in position and polarity, then calculating said score as the sum of the magnitudes of the areas of unmatched template peaks, the areas of unmatched test peaks, and the difference between the areas of any matched template and test peaks; and if peaks in said template intraventricular electrogram and said test intraventricular electrogram all match in position and polarity, then calculating said score as the sum of the magnitudes of the differences between the areas of the matched peaks.

* * * * *